US012776405B2

(12) United States Patent
Jennewine

(10) Patent No.: US 12,776,405 B2
(45) Date of Patent: Oct. 27, 2026

(54) METHOD AND SYSTEM FOR PROVIDING INTEGRATED ANALYTE MONITORING AND INFUSION SYSTEM THERAPY MANAGEMENT

(71) Applicant: Abbott Diabetes Care Inc., Alameda, CA (US)

(72) Inventor: R. Curtis Jennewine, Portland, OR (US)

(73) Assignee: Abbott Diabetes Care Inc., Alameda, CA (US)

( * ) Notice: Subject to any disclaimer, the term of this patent is extended or adjusted under 35 U.S.C. 154(b) by 188 days.

(21) Appl. No.: 18/627,221

(22) Filed: Apr. 4, 2024

(65) Prior Publication Data

US 2024/0249812 A1 Jul. 25, 2024

Related U.S. Application Data

(63) Continuation of application No. 16/273,529, filed on Feb. 12, 2019, now Pat. No. 11,967,408, which is a (Continued)

(51) Int. Cl.

| | |
|---|---|
| ***G16H 20/17*** | (2018.01) |
| ***A61B 5/00*** | (2006.01) |
| ***A61B 5/145*** | (2006.01) |
| ***A61B 5/1468*** | (2006.01) |
| ***A61B 5/1473*** | (2006.01) |

(Continued)

(52) U.S. Cl.
CPC ......... *G16H 20/17* (2018.01); *A61B 5/14532* (2013.01); *A61B 5/1468* (2013.01); *A61B 5/1473* (2013.01); *A61B 5/4839* (2013.01); *A61B 5/4848* (2013.01); *A61B 5/7275* (2013.01); *A61B 5/742* (2013.01); *A61M 5/1723* (2013.01); *A61B 5/0002* (2013.01); (Continued)

(58) Field of Classification Search
CPC ........ G16H 20/17; G16H 40/63; G16H 40/67; A61B 5/14532; A61B 5/1468; A61B 5/1473; A61B 5/4839; A61B 5/4848; A61B 5/7275; A61B 5/742; A61B 5/0002; A61M 5/1723; A61M 2230/201
See application file for complete search history.

(56) References Cited

U.S. PATENT DOCUMENTS

| | | | |
|---|---|---|---|
| 3,208,121 | A | 9/1965 | Price |
| 3,923,060 | A | 12/1975 | Ellinwood, Jr. |

(Continued)

FOREIGN PATENT DOCUMENTS

| | | | |
|---|---|---|---|
| AU | 2003259741 | B2 | 10/2008 |
| CA | 2555749 | A1 | 9/2005 |

(Continued)

OTHER PUBLICATIONS

Bremer, T. M., et al., "Benchmark Data from the Literature for Evaluation of New Glucose Sensing Technologies", Diabetes Technology & Therapeutics vol. 3 No. 3, 2001, pp. 409-418.

(Continued)

*Primary Examiner* — Navin Natnithithadha
(74) *Attorney, Agent, or Firm* — Sterne, Kessler, Goldstein & Fox P.L.L.C.

(57) ABSTRACT

Method and system for providing diabetes management and insulin therapy based on substantially real time glucose monitoring system is provided.

20 Claims, 5 Drawing Sheets

Related U.S. Application Data continuation of application No. 14/263,996, filed on Apr. 28, 2014, now Pat. No. 10,206,629, which is a continuation of application No. 13/532,346, filed on Jun. 25, 2012, now Pat. No. 8,727,982, which is a continuation of application No. 11/462,974, filed on Aug. 7, 2006, now Pat. No. 8,206,296.

(51) Int. Cl.
*A61M 5/172* (2006.01)
*G16H 40/63* (2018.01)
*G16H 40/67* (2018.01)

(52) U.S. Cl.
CPC ....... *A61M 2230/201* (2013.01); *G16H 40/63* (2018.01); *G16H 40/67* (2018.01)

(56) References Cited

U.S. PATENT DOCUMENTS

| | | | |
|---|---|---|---|
| 3,924,819 | A | 12/1975 | Lapinskas |
| 4,003,379 | A | 1/1977 | Ellinwood, Jr. |
| 4,055,175 | A | 10/1977 | Clemens et al. |
| 4,076,182 | A | 2/1978 | Stites |
| 4,151,845 | A | 5/1979 | Clemens |
| 4,360,019 | A | 11/1982 | Portner et al. |
| 4,387,863 | A | 6/1983 | Edmonston et al. |
| 4,441,968 | A | 4/1984 | Emmer et al. |
| 4,464,170 | A | 8/1984 | Clemens et al. |
| 4,601,707 | A | 7/1986 | Albisser et al. |
| 4,629,145 | A | 12/1986 | Graham |
| 4,667,896 | A | 5/1987 | Frey et al. |
| 4,685,903 | A | 8/1987 | Cable et al. |
| 4,725,010 | A | 2/1988 | Lothamer |
| 4,802,638 | A | 2/1989 | Burger et al. |
| 4,847,785 | A | 7/1989 | Stephens |
| 4,886,505 | A | 12/1989 | Haynes et al. |
| 5,019,096 | A | 5/1991 | Fox, Jr. et al. |
| 5,051,688 | A | 9/1991 | Murase et al. |
| 5,067,665 | A | 11/1991 | LoStracco et al. |
| 5,097,834 | A | 3/1992 | Skrabal |
| 5,109,577 | A | 5/1992 | Young |
| 5,135,004 | A | 8/1992 | Adams et al. |
| 5,202,261 | A | 4/1993 | Musho et al. |
| 5,209,414 | A | 5/1993 | Clemens et al. |
| 5,210,778 | A | 5/1993 | Massart |
| 5,228,449 | A | 7/1993 | Christ et al. |
| 5,231,988 | A | 8/1993 | Wernicke et al. |
| 5,236,143 | A | 8/1993 | Dragon |
| 5,237,993 | A | 8/1993 | Skrabal |
| 5,250,023 | A | 10/1993 | Lee et al. |
| 5,251,126 | A | 10/1993 | Kahn et al. |
| 5,266,359 | A | 11/1993 | Spielvogel |
| 5,284,425 | A | 2/1994 | Holtermann et al. |
| 5,344,411 | A | 9/1994 | Domb et al. |
| 5,349,852 | A | 9/1994 | Kamen et al. |
| 5,384,547 | A | 1/1995 | Lynk, Jr. et al. |
| 5,390,671 | A | 2/1995 | Lord et al. |
| 5,394,877 | A | 3/1995 | Orr et al. |
| 5,402,780 | A | 4/1995 | Faasse, Jr. |
| 5,410,326 | A | 4/1995 | Goldstein |
| 5,437,656 | A | 8/1995 | Shikani et al. |
| 5,451,424 | A | 9/1995 | Solomon et al. |
| 5,515,390 | A | 5/1996 | Benton |
| 5,526,844 | A | 6/1996 | Kamen et al. |
| 5,533,389 | A | 7/1996 | Kamen et al. |
| 5,552,997 | A | 9/1996 | Massart |
| 5,558,640 | A | 9/1996 | Pfeiler et al. |
| 5,569,186 | A | 10/1996 | Lord et al. |
| 5,593,852 | A | 1/1997 | Heller et al. |
| 5,599,321 | A | 2/1997 | Conway et al. |
| 5,601,435 | A | 2/1997 | Quy |
| 5,609,575 | A | 3/1997 | Larson et al. |
| 5,662,904 | A | 9/1997 | Ferguson et al. |
| 5,665,065 | A | 9/1997 | Colman et al. |
| 5,673,691 | A | 10/1997 | Abrams et al. |
| 5,726,646 | A | 3/1998 | Bane et al. |
| 5,738,220 | A | 4/1998 | Geszler |
| 5,748,103 | A | 5/1998 | Flach et al. |
| 5,807,375 | A | 9/1998 | Gross et al. |
| 5,822,715 | A | 10/1998 | Worthington et al. |
| 5,833,603 | A | 11/1998 | Kovacs et al. |
| 5,899,855 | A | 5/1999 | Brown |
| 5,918,603 | A | 7/1999 | Brown |
| 5,925,021 | A | 7/1999 | Castellano et al. |
| 5,951,521 | A | 9/1999 | Mastrototaro et al. |
| 5,954,643 | A | 9/1999 | VanAntwerp et al. |
| 5,956,501 | A | 9/1999 | Brown |
| 5,975,120 | A | 11/1999 | Novosel |
| 5,987,353 | A | 11/1999 | Khatchatrian et al. |
| 5,988,545 | A | 11/1999 | King |
| 6,028,413 | A | 2/2000 | Brockmann |
| 6,052,565 | A | 4/2000 | Ishikura et al. |
| 6,066,243 | A | 5/2000 | Anderson et al. |
| 6,083,248 | A | 7/2000 | Thompson |
| 6,091,975 | A | 7/2000 | Daddona et al. |
| 6,096,364 | A | 8/2000 | Bok et al. |
| 6,129,823 | A | 10/2000 | Hughes et al. |
| 6,134,461 | A | 10/2000 | Say et al. |
| 6,141,573 | A | 10/2000 | Kurnik et al. |
| 6,143,164 | A | 11/2000 | Heller et al. |
| 6,175,752 | B1 | 1/2001 | Say et al. |
| 6,233,539 | B1 | 5/2001 | Brown |
| 6,247,664 | B1 | 6/2001 | Petersen et al. |
| 6,248,067 | B1 | 6/2001 | Causey, III et al. |
| 6,254,586 | B1 | 7/2001 | Mann et al. |
| 6,270,455 | B1 | 8/2001 | Brown |
| 6,284,478 | B1 | 9/2001 | Heller et al. |
| 6,314,317 | B1 | 11/2001 | Willis |
| 6,359,270 | B1 | 3/2002 | Bridson |
| 6,379,301 | B1 | 4/2002 | Worthington et al. |
| 6,387,048 | B1 | 5/2002 | Schulman et al. |
| 6,418,332 | B1 | 7/2002 | Mastrototaro et al. |
| 6,427,088 | B1 | 7/2002 | Bowman, IV et al. |
| 6,471,689 | B1 | 10/2002 | Joseph et al. |
| 6,482,156 | B2 | 11/2002 | Iliff |
| 6,484,045 | B1 | 11/2002 | Holker et al. |
| 6,485,461 | B1 | 11/2002 | Mason et al. |
| 6,493,069 | B1 | 12/2002 | Nagashimada et al. |
| 6,498,043 | B1 | 12/2002 | Schulman et al. |
| 6,544,212 | B2 | 4/2003 | Galley et al. |
| 6,546,268 | B1 | 4/2003 | Ishikawa et al. |
| 6,554,798 | B1 | 4/2003 | Mann et al. |
| 6,558,320 | B1 | 5/2003 | Causey, III et al. |
| 6,558,321 | B1 | 5/2003 | Burd et al. |
| 6,558,351 | B1 | 5/2003 | Steil et al. |
| 6,562,001 | B2 | 5/2003 | Lebel et al. |
| 6,564,105 | B2 | 5/2003 | Starkweather et al. |
| 6,571,128 | B2 | 5/2003 | Lebel et al. |
| 6,572,542 | B1 | 6/2003 | Houben et al. |
| 6,576,101 | B1 | 6/2003 | Heller et al. |
| 6,577,899 | B2 | 6/2003 | Lebel et al. |
| 6,585,644 | B2 | 7/2003 | Lebel et al. |
| 6,598,824 | B2 | 7/2003 | Schmidt |
| 6,635,014 | B2 | 10/2003 | Starkweather et al. |
| 6,641,533 | B2 | 11/2003 | Causey, III et al. |
| 6,641,562 | B1 | 11/2003 | Peterson |
| 6,648,821 | B2 | 11/2003 | Lebel et al. |
| 6,656,114 | B1 | 12/2003 | Poulsen et al. |
| 6,656,158 | B2 | 12/2003 | Mahoney et al. |
| 6,656,159 | B2 | 12/2003 | Flaherty |
| 6,658,396 | B1 | 12/2003 | Tang et al. |
| 6,659,948 | B2 | 12/2003 | Lebel et al. |
| 6,668,196 | B1 | 12/2003 | Villegas et al. |
| 6,669,669 | B2 | 12/2003 | Flaherty et al. |
| 6,676,816 | B2 | 1/2004 | Mao et al. |
| 6,687,546 | B2 | 2/2004 | Lebel et al. |
| 6,692,457 | B2 | 2/2004 | Flaherty |
| 6,694,191 | B2 | 2/2004 | Starkweather et al. |
| 6,699,218 | B2 | 3/2004 | Flaherty et al. |
| 6,702,857 | B2 | 3/2004 | Brauker et al. |
| 6,723,072 | B2 | 4/2004 | Flaherty et al. |
| 6,733,446 | B2 | 5/2004 | Lebel et al. |
| 6,736,797 | B1 | 5/2004 | Larsen et al. |

(56) References Cited

U.S. PATENT DOCUMENTS 6,740,059 B2 5/2004 Flaherty
6,740,075 B2 5/2004 Lebel et al.
6,741,877 B1 5/2004 Shults et al.
6,744,350 B2 6/2004 Blomquist
6,749,587 B2 6/2004 Flaherty
6,758,810 B2 7/2004 Lebel et al.
6,768,425 B2 7/2004 Flaherty et al.
6,789,195 B1 9/2004 Prihoda et al.
6,810,290 B2 10/2004 Lebel et al.
6,811,533 B2 11/2004 Lebel et al.
6,811,534 B2 11/2004 Bowman, IV et al.
6,813,519 B2 11/2004 Lebel et al.
6,827,702 B2 * 12/2004 Lebel ................ A61M 5/14276 604/67
6,830,558 B2 12/2004 Flaherty et al.
6,837,858 B2 1/2005 Cunningham et al.
6,850,790 B2 2/2005 Berner et al.
6,852,104 B2 2/2005 Blomquist
6,862,465 B2 3/2005 Shults et al.
6,873,268 B2 3/2005 Lebel et al.
6,882,940 B2 4/2005 Potts et al.
6,887,270 B2 5/2005 Miller et al.
6,896,666 B2 5/2005 Kochamba
6,902,207 B2 6/2005 Lickliter
6,916,159 B2 7/2005 Rush et al.
6,923,763 B1 8/2005 Kovatchev et al.
6,931,327 B2 8/2005 Goode, Jr. et al.
6,936,006 B2 8/2005 Sabra
6,946,446 B2 9/2005 Ma et al.
6,950,708 B2 9/2005 Bowman, IV et al.
6,958,705 B2 10/2005 Lebel et al.
6,960,192 B1 11/2005 Flaherty et al.
6,974,437 B2 12/2005 Lebel et al.
6,999,854 B2 2/2006 Roth
7,003,336 B2 2/2006 Holker et al.
7,015,817 B2 3/2006 Copley et al.
7,016,713 B2 3/2006 Gardner et al.
7,018,360 B2 3/2006 Flaherty et al.
7,024,245 B2 4/2006 Lebel et al.
7,027,848 B2 4/2006 Robinson et al.
7,027,931 B1 4/2006 Jones et al.
7,029,455 B2 4/2006 Flaherty
7,034,677 B2 4/2006 Steinthal et al.
7,041,468 B2 5/2006 Drucker et al.
7,046,153 B2 5/2006 Oja et al.
7,052,251 B2 5/2006 Nason et al.
7,052,472 B1 5/2006 Miller et al.
7,066,922 B2 6/2006 Angel et al.
7,074,307 B2 7/2006 Simpson et al.
7,077,328 B2 7/2006 Krishnaswamy et al.
7,079,977 B2 7/2006 Osorio et al.
7,081,195 B2 7/2006 Simpson et al.
7,092,891 B2 8/2006 Maus et al.
7,108,778 B2 9/2006 Simpson et al.
7,110,803 B2 9/2006 Shults et al.
7,113,821 B1 9/2006 Sun et al.
7,133,717 B2 11/2006 Coston et al.
7,134,999 B2 11/2006 Brauker et al.
7,136,689 B2 11/2006 Shults et al.
7,137,964 B2 11/2006 Flaherty
7,144,384 B2 12/2006 Gorman et al.
7,153,265 B2 12/2006 Vachon
7,155,112 B2 12/2006 Uno et al.
7,155,290 B2 12/2006 Von Arx et al.
7,167,818 B2 1/2007 Brown
7,171,274 B2 1/2007 Starkweather et al.
7,171,312 B2 1/2007 Steinthal et al.
7,179,226 B2 2/2007 Crothall et al.
7,192,450 B2 3/2007 Brauker et al.
7,207,974 B2 4/2007 Safabash et al.
7,216,665 B1 5/2007 Sims, Jr.
7,226,278 B2 6/2007 Nason et al.
7,226,442 B2 6/2007 Sheppard, Jr. et al.
7,226,978 B2 6/2007 Tapsak et al.
7,229,042 B2 6/2007 Thebault et al.
7,267,665 B2 9/2007 Steil et al.
7,276,029 B2 10/2007 Goode, Jr. et al.
7,286,894 B1 10/2007 Grant et al.
7,303,549 B2 12/2007 Flaherty et al.
7,310,544 B2 12/2007 Brister et al.
7,318,816 B2 1/2008 Bobroff et al.
7,324,012 B2 1/2008 Mann et al.
7,329,239 B2 2/2008 Safabash et al.
7,335,294 B2 2/2008 Heller et al.
7,354,420 B2 4/2008 Steil et al.
7,364,568 B2 4/2008 Angel et al.
7,364,592 B2 4/2008 Carr-Brendel et al.
7,366,556 B2 4/2008 Brister et al.
7,379,765 B2 5/2008 Petisce et al.
7,381,184 B2 6/2008 Funderburk et al.
7,402,153 B2 7/2008 Steil et al.
7,404,796 B2 7/2008 Ginsberg
7,424,318 B2 9/2008 Brister et al.
7,429,258 B2 9/2008 Angel et al.
7,455,663 B2 11/2008 Bikovsky
7,460,898 B2 12/2008 Brister et al.
7,462,264 B2 12/2008 Heller et al.
7,467,003 B2 12/2008 Brister et al.
7,471,972 B2 12/2008 Rhodes et al.
7,483,736 B2 1/2009 Marchitto et al.
7,494,465 B2 2/2009 Brister et al.
7,497,827 B2 3/2009 Brister et al.
7,499,002 B2 3/2009 Blasko et al.
7,519,408 B2 4/2009 Rasdal et al.
7,547,281 B2 6/2009 Hayes et al.
7,583,990 B2 9/2009 Goode, Jr. et al.
7,591,801 B2 9/2009 Brauker et al.
7,599,726 B2 10/2009 Goode, Jr. et al.
7,613,491 B2 11/2009 Boock et al.
7,615,007 B2 11/2009 Shults et al.
7,630,748 B2 12/2009 Budiman
7,632,228 B2 12/2009 Brauker et al.
7,637,868 B2 12/2009 Saint et al.
7,640,048 B2 12/2009 Dobbles et al.
7,645,263 B2 1/2010 Angel et al.
7,651,596 B2 1/2010 Petisce et al.
7,651,845 B2 1/2010 Doyle, III et al.
7,654,956 B2 2/2010 Brister et al.
7,657,297 B2 2/2010 Simpson et al.
7,697,967 B2 4/2010 Stafford
7,699,775 B2 4/2010 Desai et al.
7,711,402 B2 5/2010 Shults et al.
7,713,574 B2 5/2010 Brister et al.
7,715,893 B2 5/2010 Kamath et al.
7,727,147 B1 6/2010 Osorio et al.
7,731,657 B2 6/2010 Stafford
7,736,344 B2 6/2010 Moberg et al.
7,763,042 B2 7/2010 Iio et al.
7,766,829 B2 8/2010 Sloan et al.
7,768,387 B2 8/2010 Fennell
7,783,333 B2 8/2010 Brister et al.
7,792,562 B2 9/2010 Shults et al.
7,813,809 B2 10/2010 Strother et al.
7,822,454 B1 10/2010 Alden et al.
7,826,981 B2 11/2010 Goode, Jr. et al.
7,889,069 B2 2/2011 Fifolt et al.
7,899,511 B2 3/2011 Shults et al.
7,899,545 B2 3/2011 John
7,905,833 B2 3/2011 Brister et al.
7,914,450 B2 3/2011 Goode, Jr. et al.
7,938,797 B2 5/2011 Estes
7,941,200 B2 5/2011 Weinert et al.
7,946,985 B2 5/2011 Mastrototaro et al.
7,970,448 B2 6/2011 Shults et al.
7,972,296 B2 7/2011 Braig et al.
7,974,672 B2 7/2011 Shults et al.
7,976,466 B2 7/2011 Ward et al.
7,978,063 B2 7/2011 Baldus et al.
8,010,174 B2 8/2011 Goode, Jr. et al.
8,010,256 B2 8/2011 Oowada
8,105,268 B2 * 1/2012 Lebel .................... A61M 5/172 604/66
RE43,316 E 4/2012 Brown et al.
8,192,394 B2 6/2012 Estes et al.

(56) References Cited

U.S. PATENT DOCUMENTS 8,206,296 B2 6/2012 Jennewine
8,216,138 B1 7/2012 McGarraugh
8,282,549 B2 10/2012 Brauker et al.
8,461,985 B2 6/2013 Fennell et al.
8,597,570 B2 12/2013 Terashima et al.
8,727,982 B2 5/2014 Jennewine
8,732,188 B2 5/2014 Doniger et al.
10,206,629 B2 2/2019 Jennewine
10,685,749 B2 6/2020 Hayter et al.
11,749,410 B2 9/2023 Hayter et al.
2001/0020124 A1 9/2001 Tamada
2001/0037366 A1 11/2001 Webb et al.
2001/0047604 A1 12/2001 Valiulis
2002/0016719 A1 2/2002 Nemeth et al.
2002/0019612 A1 2/2002 Watanabe et al.
2002/0054320 A1 5/2002 Ogino
2002/0095076 A1 7/2002 Krausman et al.
2002/0106709 A1 8/2002 Potts et al.
2002/0107476 A1 8/2002 Mann et al.
2002/0133107 A1 9/2002 Darcey
2002/0147135 A1 10/2002 Schnell
2002/0169439 A1 11/2002 Flaherty
2002/0169635 A1 11/2002 Shillingburg
2002/0193679 A1 12/2002 Malave et al.
2003/0021729 A1 1/2003 Moller et al.
2003/0023317 A1 1/2003 Brauker et al.
2003/0028089 A1 2/2003 Galley et al.
2003/0032874 A1 2/2003 Rhodes et al.
2003/0050621 A1* 3/2003 Lebel .................... A61M 5/172 128/920
2003/0055380 A1 3/2003 Flaherty
2003/0060692 A1 3/2003 L. Ruchti et al.
2003/0060753 A1 3/2003 Starkweather et al.
2003/0065308 A1 4/2003 Lebel et al.
2003/0069541 A1 4/2003 Gillis et al.
2003/0073414 A1 4/2003 P. Capps
2003/0100040 A1 5/2003 Bonnecaze et al.
2003/0114836 A1 6/2003 Estes et al.
2003/0114897 A1 6/2003 Von Arx et al.
2003/0122021 A1 7/2003 McConnell et al.
2003/0130616 A1 7/2003 Steil et al.
2003/0144362 A1 7/2003 Utterberg et al.
2003/0147515 A1 8/2003 Kai et al.
2003/0167035 A1 9/2003 Flaherty et al.
2003/0175323 A1 9/2003 Utterberg et al.
2003/0176933 A1 9/2003 Lebel et al.
2003/0212379 A1 11/2003 Bylund et al.
2003/0217966 A1 11/2003 Tapsak et al.
2003/0225361 A1 12/2003 Sabra
2004/0010207 A1 1/2004 Flaherty et al.
2004/0011671 A1 1/2004 Shults et al.
2004/0015131 A1 1/2004 Flaherty et al.
2004/0041749 A1 3/2004 Dixon
2004/0045879 A1 3/2004 Shults et al.
2004/0063435 A1 4/2004 Sakamoto et al.
2004/0064088 A1 4/2004 Gorman et al.
2004/0064096 A1 4/2004 Flaherty et al.
2004/0099529 A1 5/2004 Mao et al.
2004/0122530 A1 6/2004 Hansen et al.
2004/0133390 A1 7/2004 Osorio et al.
2004/0135684 A1 7/2004 Steinthal et al.
2004/0147872 A1 7/2004 Thompson
2004/0152622 A1 8/2004 Keith et al.
2004/0153032 A1 8/2004 Garribotto et al.
2004/0155770 A1 8/2004 Nelson et al.
2004/0162521 A1 8/2004 Bengtsson
2004/0167464 A1 8/2004 Ireland et al.
2004/0172307 A1 9/2004 Gruber
2004/0186362 A1 9/2004 Brauker et al.
2004/0193025 A1 9/2004 Steil et al.
2004/0193090 A1 9/2004 Lebel et al.
2004/0199059 A1 10/2004 Brauker et al.
2004/0204868 A1 10/2004 Maynard et al.
2004/0210180 A1 10/2004 Altman
2004/0210208 A1 10/2004 Paul et al.
2004/0225338 A1 11/2004 Lebel et al.
2004/0254433 A1 12/2004 Bandis et al.
2004/0260478 A1 12/2004 Schwamm
2005/0001024 A1 1/2005 Kusaka et al.
2005/0004439 A1 1/2005 Shin et al.
2005/0010269 A1 1/2005 Lebel et al.
2005/0027180 A1 2/2005 Goode, Jr. et al.
2005/0031689 A1 2/2005 Shults et al.
2005/0038332 A1 2/2005 Saidara et al.
2005/0038674 A1 2/2005 Braig et al.
2005/0043598 A1 2/2005 Goode, Jr. et al.
2005/0049179 A1 3/2005 Davidson et al.
2005/0065464 A1 3/2005 Talbot et al.
2005/0065465 A1* 3/2005 Lebel .................... A61M 5/172 604/66
2005/0070774 A1 3/2005 Addison et al.
2005/0090607 A1 4/2005 Tapsak et al.
2005/0096511 A1 5/2005 Fox et al.
2005/0096516 A1 5/2005 Soykan et al.
2005/0112169 A1 5/2005 Brauker et al.
2005/0113653 A1 5/2005 Fox et al.
2005/0113886 A1 5/2005 Fischell et al.
2005/0116683 A1 6/2005 Cheng et al.
2005/0119540 A1 6/2005 Potts et al.
2005/0137530 A1 6/2005 Campbell et al.
2005/0143635 A1 6/2005 Kamath et al.
2005/0171512 A1 8/2005 Flaherty
2005/0176136 A1 8/2005 Burd et al.
2005/0181010 A1 8/2005 Hunter et al.
2005/0182306 A1 8/2005 Sloan
2005/0182358 A1 8/2005 Veit et al.
2005/0182366 A1 8/2005 Vogt et al.
2005/0187442 A1 8/2005 Cho et al.
2005/0187720 A1 8/2005 Goode, Jr. et al.
2005/0192557 A1 9/2005 Brauker et al.
2005/0195930 A1 9/2005 Spital et al.
2005/0203360 A1 9/2005 Brauker et al.
2005/0203461 A1 9/2005 Flaherty et al.
2005/0204134 A1 9/2005 Von Arx et al.
2005/0214892 A1 9/2005 Kovatchev et al.
2005/0238507 A1 10/2005 Diianni et al.
2005/0245795 A1 11/2005 Goode, Jr. et al.
2005/0245799 A1 11/2005 Brauker et al.
2005/0251033 A1 11/2005 Scarantino et al.
2005/0261667 A1 11/2005 Crank et al.
2005/0277872 A1 12/2005 Colby, Jr. et al.
2005/0277912 A1 12/2005 John
2006/0001551 A1 1/2006 Kraft et al.
2006/0004603 A1 1/2006 Peterka et al.
2006/0010098 A1 1/2006 Goodnow et al.
2006/0015020 A1 1/2006 Neale et al.
2006/0016700 A1 1/2006 Brister et al.
2006/0017923 A1 1/2006 Ruchti et al.
2006/0019327 A1 1/2006 Brister et al.
2006/0020186 A1 1/2006 Brister et al.
2006/0020187 A1 1/2006 Brister et al.
2006/0020188 A1 1/2006 Kamath et al.
2006/0020189 A1 1/2006 Brister et al.
2006/0020190 A1 1/2006 Kamath et al.
2006/0020191 A1 1/2006 Brister et al.
2006/0020192 A1 1/2006 Brister et al.
2006/0020300 A1 1/2006 Nghiem et al.
2006/0036139 A1 2/2006 Brister et al.
2006/0036140 A1 2/2006 Brister et al.
2006/0036141 A1 2/2006 Kamath et al.
2006/0036142 A1 2/2006 Brister et al.
2006/0036143 A1 2/2006 Brister et al.
2006/0036144 A1 2/2006 Brister et al.
2006/0036145 A1 2/2006 Brister et al.
2006/0041229 A1 2/2006 Garibotto et al.
2006/0065772 A1 3/2006 Grant et al.
2006/0079740 A1 4/2006 Silver et al.
2006/0091006 A1 5/2006 Wang et al.
2006/0095020 A1 5/2006 Casas et al.
2006/0142651 A1 6/2006 Brister et al.
2006/0154642 A1 7/2006 Scannell, Jr.
2006/0166629 A1 7/2006 Reggiardo
2006/0173406 A1 8/2006 Hayes et al.
2006/0173444 A1 8/2006 Choy et al.

(56) References Cited

U.S. PATENT DOCUMENTS

2006/0173712 A1 8/2006 Joubert
2006/0178633 A1 8/2006 Garibotto et al.
2006/0189863 A1 8/2006 Peyser et al.
2006/0193375 A1 8/2006 Lee
2006/0202805 A1 9/2006 Schulman et al.
2006/0222566 A1 10/2006 Brauker et al.
2006/0224141 A1 10/2006 Rush et al.
2006/0226985 A1 10/2006 Goodnow et al.
2006/0247508 A1 11/2006 Fennell
2006/0258929 A1 11/2006 Goode, Jr. et al.
2006/0272652 A1 12/2006 Stocker et al.
2006/0276771 A1 12/2006 Galley et al.
2006/0282290 A1 12/2006 Flaherty et al.
2006/0290496 A1 12/2006 Peeters
2006/0293577 A1 12/2006 Morrison et al.
2006/0293607 A1 12/2006 Alt et al.
2007/0016381 A1 1/2007 Kamath et al.
2007/0016449 A1 1/2007 Cohen et al.
2007/0017983 A1 1/2007 Frank et al.
2007/0027381 A1 2/2007 Stafford
2007/0032717 A1 2/2007 Brister et al.
2007/0033074 A1 2/2007 Nitzan et al.
2007/0060869 A1 3/2007 Tolle et al.
2007/0060870 A1 3/2007 Tolle et al.
2007/0060871 A1 3/2007 Istoc et al.
2007/0060979 A1 3/2007 Strother et al.
2007/0066956 A1 3/2007 Finkel
2007/0073129 A1 3/2007 Shah et al.
2007/0078320 A1 4/2007 Stafford
2007/0078321 A1 4/2007 Mazza et al.
2007/0078322 A1 4/2007 Stafford
2007/0078818 A1 4/2007 Zivitz et al.
2007/0093786 A1 4/2007 Goldsmith et al.
2007/0100222 A1 5/2007 Mastrototaro et al.
2007/0106135 A1 5/2007 Sloan et al.
2007/0118405 A1 5/2007 Campbell et al.
2007/0128682 A1 6/2007 Rosman et al.
2007/0129621 A1 6/2007 Kellogg et al.
2007/0149874 A1 6/2007 Say et al.
2007/0149875 A1 6/2007 Ouyang et al.
2007/0163880 A1 7/2007 Woo et al.
2007/0179370 A1 8/2007 Say et al.
2007/0191702 A1 8/2007 Yodfat et al.
2007/0203407 A1 8/2007 Hoss et al.
2007/0203966 A1 8/2007 Brauker et al.
2007/0208244 A1 9/2007 Brauker et al.
2007/0208246 A1 9/2007 Brauker et al.
2007/0213657 A1 9/2007 Jennewine et al.
2007/0219480 A1 9/2007 Kamen et al.
2007/0219597 A1 9/2007 Kamen et al.
2007/0228071 A1 10/2007 Kamen et al.
2007/0235331 A1 10/2007 Simpson et al.
2007/0249922 A1 10/2007 Peyser et al.
2007/0255114 A1 11/2007 Ackermann et al.
2007/0255321 A1 11/2007 Gerber et al.
2007/0255348 A1 11/2007 Holtzclaw
2007/0282299 A1 12/2007 Hellwig
2007/0299409 A1 12/2007 Whitbourne et al.
2008/0004515 A1 1/2008 Jennewine
2008/0004601 A1 1/2008 Jennewine et al.
2008/0009692 A1 1/2008 Stafford
2008/0018480 A1 1/2008 Sham
2008/0021436 A1 1/2008 Wolpert et al.
2008/0021666 A1 1/2008 Goode, Jr. et al.
2008/0033254 A1 2/2008 Kamath et al.
2008/0033268 A1 2/2008 Stafford
2008/0039702 A1 2/2008 Hayter et al.
2008/0045824 A1 2/2008 Tapsak et al.
2008/0058773 A1 3/2008 John
2008/0060955 A1 3/2008 Goodnow
2008/0061961 A1 3/2008 John
2008/0064937 A1 3/2008 McGarraugh et al.
2008/0071156 A1 3/2008 Brister et al.
2008/0083617 A1 4/2008 Simpson et al.
2008/0086042 A1 4/2008 Brister et al.
2008/0086044 A1 4/2008 Brister et al.
2008/0086273 A1 4/2008 Shults et al.
2008/0092638 A1 4/2008 Brenneman et al.
2008/0093447 A1 4/2008 Johnson et al.
2008/0097246 A1 4/2008 Stafford
2008/0108942 A1 5/2008 Brister et al.
2008/0114228 A1 5/2008 McCluskey et al.
2008/0119707 A1 5/2008 Stafford
2008/0139910 A1 6/2008 Mastrototaro et al.
2008/0177149 A1 7/2008 Weinert et al.
2008/0183061 A1 7/2008 Goode et al.
2008/0183399 A1 7/2008 Goode et al.
2008/0188731 A1 8/2008 Brister et al.
2008/0189051 A1 8/2008 Goode et al.
2008/0194934 A1 8/2008 Ray et al.
2008/0194935 A1 8/2008 Brister et al.
2008/0194936 A1 8/2008 Goode et al.
2008/0194937 A1 8/2008 Goode et al.
2008/0194938 A1 8/2008 Brister et al.
2008/0195232 A1 8/2008 Carr-Brendel et al.
2008/0195967 A1 8/2008 Goode et al.
2008/0197024 A1 8/2008 Simpson et al.
2008/0200788 A1 8/2008 Brister et al.
2008/0200789 A1 8/2008 Brister et al.
2008/0200791 A1 8/2008 Simpson et al.
2008/0200897 A1 8/2008 Hoss et al.
2008/0201325 A1 8/2008 Doniger et al.
2008/0208025 A1 8/2008 Shults et al.
2008/0214915 A1 9/2008 Brister et al.
2008/0214918 A1 9/2008 Brister et al.
2008/0228051 A1 9/2008 Shults et al.
2008/0228054 A1 9/2008 Shults et al.
2008/0228055 A1 9/2008 Sher
2008/0234663 A1 9/2008 Yodfat et al.
2008/0234943 A1 9/2008 Ray et al.
2008/0242961 A1 10/2008 Brister et al.
2008/0242963 A1 10/2008 Essenpreis et al.
2008/0254544 A1 10/2008 Modzelewski et al.
2008/0262469 A1 10/2008 Brister et al.
2008/0269687 A1 10/2008 Chong et al.
2008/0269714 A1 10/2008 Mastrototaro et al.
2008/0269723 A1 10/2008 Mastrototaro et al.
2008/0275313 A1 11/2008 Brister et al.
2008/0287764 A1 11/2008 Rasdal et al.
2008/0287765 A1 11/2008 Rasdal et al.
2008/0287766 A1 11/2008 Rasdal et al.
2008/0296155 A1 12/2008 Shults et al.
2008/0300572 A1 12/2008 Rankers et al.
2008/0306368 A1 12/2008 Goode, Jr. et al.
2008/0306434 A1 12/2008 Dobbles et al.
2008/0306435 A1 12/2008 Kamath et al.
2008/0306444 A1 12/2008 Brister et al.
2008/0319085 A1 12/2008 Wright et al.
2009/0005666 A1 1/2009 Shin et al.
2009/0006133 A1 1/2009 Weinert et al.
2009/0012379 A1 1/2009 Goode, Jr. et al.
2009/0018424 A1 1/2009 Kamath et al.
2009/0030294 A1 1/2009 Petisce et al.
2009/0036758 A1 2/2009 Brauker et al.
2009/0036763 A1 2/2009 Brauker et al.
2009/0040022 A1 2/2009 Finkenzeller
2009/0043181 A1 2/2009 Brauker et al.
2009/0043182 A1 2/2009 Brauker et al.
2009/0043525 A1 2/2009 Brauker et al.
2009/0043541 A1 2/2009 Brauker et al.
2009/0043542 A1 2/2009 Brauker et al.
2009/0045055 A1 2/2009 Rhodes et al.
2009/0048503 A1 2/2009 Dalal et al.
2009/0054747 A1 2/2009 Fennell
2009/0054748 A1 2/2009 Feldman
2009/0054750 A1 2/2009 Jennewine
2009/0062633 A1 3/2009 Brauker et al.
2009/0062635 A1 3/2009 Brauker et al.
2009/0069650 A1 3/2009 Jennewine
2009/0076356 A1 3/2009 Simpson et al.
2009/0076359 A1 3/2009 Peyser
2009/0076360 A1 3/2009 Brister et al.
2009/0076361 A1 3/2009 Kamath et al.
2009/0082693 A1 3/2009 Stafford

(56) References Cited

U.S. PATENT DOCUMENTS

2009/0085873 A1 4/2009 Betts et al.
2009/0088614 A1 4/2009 Taub
2009/0088787 A1 4/2009 Koike et al.
2009/0093687 A1 4/2009 Telfort et al.
2009/0099436 A1 4/2009 Brister et al.
2009/0102678 A1 4/2009 Mazza et al.
2009/0105560 A1 4/2009 Solomon
2009/0105569 A1 4/2009 Stafford
2009/0105570 A1 4/2009 Sloan et al.
2009/0105571 A1 4/2009 Fennell et al.
2009/0124877 A1 5/2009 Goode, Jr. et al.
2009/0124878 A1 5/2009 Goode, Jr. et al.
2009/0124879 A1 5/2009 Brister et al.
2009/0124964 A1 5/2009 Leach et al.
2009/0131768 A1 5/2009 Simpson et al.
2009/0131769 A1 5/2009 Leach et al.
2009/0131776 A1 5/2009 Simpson et al.
2009/0131777 A1 5/2009 Simpson et al.
2009/0137886 A1 5/2009 Shariati et al.
2009/0137887 A1 5/2009 Shariati et al.
2009/0143659 A1 6/2009 Li et al.
2009/0143660 A1 6/2009 Brister et al.
2009/0156919 A1 6/2009 Brister et al.
2009/0156924 A1 6/2009 Shariati et al.
2009/0163790 A1 6/2009 Brister et al.
2009/0163791 A1 6/2009 Brister et al.
2009/0164190 A1 6/2009 Hayter
2009/0164239 A1 6/2009 Hayter et al.
2009/0164251 A1 6/2009 Hayter
2009/0178459 A1 7/2009 Li et al.
2009/0182217 A1 7/2009 Li et al.
2009/0192366 A1 7/2009 Mensinger et al.
2009/0192380 A1 7/2009 Shariati et al.
2009/0192722 A1 7/2009 Shariati et al.
2009/0192724 A1 7/2009 Brauker et al.
2009/0192745 A1 7/2009 Kamath et al.
2009/0192751 A1 7/2009 Kamath et al.
2009/0203981 A1 8/2009 Brauker et al.
2009/0204341 A1 8/2009 Brauker et al.
2009/0216100 A1 8/2009 Ebner et al.
2009/0216102 A1 8/2009 Say et al.
2009/0216103 A1 8/2009 Brister et al.
2009/0240120 A1 9/2009 Mensinger et al.
2009/0240128 A1 9/2009 Mensinger et al.
2009/0240193 A1 9/2009 Mensinger et al.
2009/0242399 A1 10/2009 Kamath et al.
2009/0242425 A1 10/2009 Kamath et al.
2009/0247855 A1 10/2009 Boock et al.
2009/0247856 A1 10/2009 Boock et al.
2009/0247931 A1 10/2009 Damgaard-Sorensen
2009/0253973 A1 10/2009 Bashan et al.
2009/0287073 A1 11/2009 Boock et al.
2009/0287074 A1 11/2009 Shults et al.
2009/0292188 A1 11/2009 Hoss et al.
2009/0298182 A1 12/2009 Schulat et al.
2009/0299155 A1 12/2009 Yang et al.
2009/0299156 A1 12/2009 Simpson et al.
2009/0299162 A1 12/2009 Brauker et al.
2009/0299276 A1 12/2009 Brauker et al.
2010/0010324 A1 1/2010 Brauker et al.
2010/0010329 A1 1/2010 Taub et al.
2010/0010331 A1 1/2010 Brauker et al.
2010/0010332 A1 1/2010 Brauker et al.
2010/0016687 A1 1/2010 Brauker et al.
2010/0016698 A1 1/2010 Rasdal et al.
2010/0022855 A1 1/2010 Brauker et al.
2010/0030038 A1 2/2010 Brauker et al.
2010/0030053 A1 2/2010 Goode, Jr. et al.
2010/0030484 A1 2/2010 Brauker et al.
2010/0030485 A1 2/2010 Brauker et al.
2010/0036215 A1 2/2010 Goode, Jr. et al.
2010/0036216 A1 2/2010 Goode, Jr. et al.
2010/0036222 A1 2/2010 Goode, Jr. et al.
2010/0036223 A1 2/2010 Goode, Jr. et al.
2010/0036225 A1 2/2010 Goode, Jr. et al.
2010/0041971 A1 2/2010 Goode, Jr. et al.
2010/0045465 A1 2/2010 Brauker et al.
2010/0049024 A1 2/2010 Saint et al.
2010/0063373 A1 3/2010 Kamath et al.
2010/0076283 A1 3/2010 Simpson et al.
2010/0081908 A1 4/2010 Dobbles et al.
2010/0081910 A1 4/2010 Brister et al.
2010/0087724 A1 4/2010 Brauker et al.
2010/0096259 A1 4/2010 Zhang et al.
2010/0099970 A1 4/2010 Shults et al.
2010/0099971 A1 4/2010 Shults et al.
2010/0105999 A1 4/2010 Dixon et al.
2010/0119693 A1 5/2010 Tapsak et al.
2010/0121169 A1 5/2010 Petisce et al.
2010/0141656 A1 6/2010 Krieftewirth
2010/0152554 A1 6/2010 Steine et al.
2010/0160759 A1 6/2010 Celentano et al.
2010/0168538 A1 7/2010 Keenan et al.
2010/0174266 A1 7/2010 Estes
2010/0185175 A1 7/2010 Kamen et al.
2010/0191082 A1 7/2010 Brister et al.
2010/0198142 A1 8/2010 Sloan et al.
2010/0213080 A1 8/2010 Celentano et al.
2010/0240975 A1 9/2010 Goode, Jr. et al.
2010/0274111 A1 10/2010 Say et al.
2010/0292634 A1 11/2010 Kircher, Jr. et al.
2010/0312176 A1 12/2010 Lauer et al.
2010/0313105 A1 12/2010 Nekoomaram et al.
2011/0031986 A1 2/2011 Bhat et al.
2011/0077490 A1 3/2011 Simpson et al.
2011/0148905 A1 6/2011 Simmons et al.
2011/0208027 A1 8/2011 Wagner et al.
2011/0257895 A1 10/2011 Brauker et al.
2011/0287528 A1 11/2011 Fern et al.
2012/0165640 A1 6/2012 Galley et al.
2012/0173200 A1 7/2012 Breton et al.
2012/0265043 A1 10/2012 Jennewine
2013/0235166 A1 9/2013 Jones et al.
2014/0235985 A1 8/2014 Jennewine
2014/0258190 A1 9/2014 Doniger et al.
2016/0106919 A1 4/2016 Hayter et al.
2017/0193184 A1 7/2017 Hayter et al.
2019/0175119 A1 6/2019 Jennewine
2023/0154625 A1 5/2023 Hayter et al.

FOREIGN PATENT DOCUMENTS

CA 2632709 A1 6/2007
CA 2701374 C 2/2014
CA 2495648 C 7/2014
CA 2498682 C 7/2016
CA 2615575 C 7/2018
EP 1956371 A2 8/2008
EP 2260757 B1 3/2016
WO WO 1999056613 A1 11/1999
WO WO 2001052935 A1 7/2001
WO WO 2001054753 A2 8/2001
WO WO 2004009161 A1 1/2004
WO WO 2004015539 A2 2/2004
WO WO 2006037109 A2 4/2006
WO WO 2006079867 A1 8/2006
WO WO 2007065285 A2 6/2007
WO WO 2007101260 A2 9/2007
WO WO 2007149319 A2 12/2007
WO WO 2008001366 A2 1/2008
WO WO 2008003003 A2 1/2008
WO WO 2008005780 A2 1/2008
WO WO 2011104616 A2 9/2011

OTHER PUBLICATIONS

Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.
Diem, P., et al., "Clinical Performance of a Continuous Viscometric Affinity Sensor for Glucose", Diabetes Technology & Therapeutics vol. 6, 2004, pp. 790-799.

(56) References Cited

OTHER PUBLICATIONS

Exhibit CP-7, Second Expert Report of Dr. Cesar C. Palerm, Oct. 21, 2022, Garg, S. et al., "Improvement in Glycemic Excursions with a Transcutaneous, Real-Time Continuous Glucose Sensor", Diabetes Care, Jan. 2006, 29(12):44-50.
Exhibit No. 2, to the Expert Report of Professor Nick Oliver, Sep. 20, 2022, "Note for Guidance on Clinical Investigation of Medicinal Products in the Treatment of Diabetes Mellitus," The European Agency for the Evaluation of Medicinal Products, 2002, 12 pages.
Exhibit No. 3, to the Expert Report of Professor Nick Oliver, Sep. 20, 2022, "Defining and Reporting Hypoglycemia in Diabetes", American Diabetes Association, Diabetes Care, 2005, 28(5):1245-1249.
Exhibit No. 11, to the Expert Report of Professor Nick Oliver, Sep. 20, 2022, "The Effect of Intensive Treatment of Diabetes on the Development and Progression of Long-Term Complications in Insulin-Dependent Diabetes Mellitus" The New England Journal of Medicine, 1993, 329(14):977-986.
Exhibit No. 12, to the Expert Report of Professor Nick Oliver, Sep. 20, 2022, National Service Framework for Diabetes: Standards, Dept. of Health, 2002, 48 pages.
Exhibit No. 13, to the Expert Report of Professor Nick Oliver, Sep. 20, 2022, Amiel, S. et al., "Training in flexible, intensive insulin management to enable dietary freedom in people with type 1 diabetes: dose adjustment for normal eating (DAFNE) randomized controlled trial" BMJ, 2002, 325; 6 pages.
Exhibit No. 14, to the Expert Report of Professor Nick Oliver, Sep. 20, 2022, "Type 1 diabetes: diagnosis and management of type 1 diabetes in children, young people and adults" National Institute for Clinical Excellence, Clinical Guideline 15, Jul. 2004, 113 pages.
Exhibit No. 23, to the Expert Report of Professor Nick Oliver, Sep. 20, 2022, Internet Archive, WayBack Machine, Medtronic MiniMed, 2004, 20 pages.
Exhibit No. 24, to the Expert Report of Professor Nick Oliver, Sep. 20, 2022, "Glucowatch G2, Automatic Glucose Biographer and Autosensors," 2002, 70 pages.
Exhibit No. 25, to the Expert Report of Professor Nick Oliver, Sep. 20, 2022, "Guardian® Real-Time Continuous Glucose Monitoring System, User Guide," Medtronic MiniMed, 2006, 181 pages.
Exhibit No. 32, to the Expert Report of Professor Nick Oliver, Sep. 20, 2022, Puhr, S. et al., "Real-World Hypoglycemia Avoidance with a Predictive Low Glucose Alert Does Not Depend on Frequent Screen Views", Journal of Diabetes Sciences And Technology, 2004, 14(1): 83-86.
Garg, S., et al., "Improvement in Glycemic Excursions with a Transcutaneous, Real-Time Continuous Glucose Sensor", Diabetes Care, vol. 29, No. 1, 2006, pp. 44-50.
Kondepati, V., et al., "Recent Progress in Analytical Instrumentation for Glycemic Control in Diabetic and Critically Ill Patients", Analytical Bioanalytical Chemistry, vol. 388, 2007, pp. 545-563.
Kuure-Kinsey, M., et al., "A Dual-Rate Kalman Filter for Continuous Glucose Monitoring", Proceedings of the 28th IEEE, EMBS Annual International Conference, New York City, 2006, pp. 63-66.
Li, Y., et al., "In Vivo Release From a Drug Delivery MEMS Device", Journal of Controlled Release, vol. 100, 2004, 99. 211-219.
Lodwig, V., et al., "Continuous Glucose Monitoring with Glucose Sensors: Calibration and Assessment Criteria", Diabetes Technology & Theraneutics vol. 5 No. 4, 2003, pp. 573-587.
Morbiducci, U, et al., "Improved Usability of the Minimal Model of Insulin Sensitivity Based on an Automated Approach and Genetic Algorithms for Parameter Estimation", Clinical Science, vol. 112, 2007, pp. 257-263.
Mougiakakou, et al., "A Real Time Simulation Model of Glucose-Insulin Metabolism for Type 1 Diabetes Patients", Proceedin2s of the 2005 IEEE, 2005, pp. 298-301.
Panteleon, A. E., et al., "The Role of the Independent Variable to Glucose Sensor Calibration", Diabetes Technology & Therapeutics vol. 5. No. 3, 2003, pp. 401-410.
Parker, R., et al., "Robust Hoo Glucose Control in Diabetes Using a Physiological Model", AIChE Journal, vol. 46, No. 12, 2000, pp. 2537-2549.
PMA Approvals FDA—webpage available at: https://www.fda.gov; 3 pages.
PMA database search for Freestyle Navigator Continuous Glucose Monitor—https://www.fda.gov; 6 pages.
Sandham, William et al., "Blood Glucose Prediction for Diabetes Therapy Using a Recurrent Artificial Neural Network," 9th European Signal Processing Conference (EUSIPCO 1998), 1998, pp. 1-4.
U.S. Appl. No. 11/462,974, Notice of Allowance mailed Mar. 14, 2012.
U.S. Appl. No. 11/462,974, Office Action mailed Feb. 16, 2011.
U.S. Appl. No. 11/462,974, Office Action mailed Oct. 27, 2011.
U.S. Appl. No. 13/532,346, Notice of Allowance mailed Feb. 25, 2014.
U.S. Appl. No. 13/532,346, Office Action mailed Jan. 17, 2014.

* cited by examiner

100

120

METHOD AND SYSTEM FOR PROVIDING INTEGRATED ANALYTE MONITORING AND INFUSION SYSTEM THERAPY MANAGEMENT

RELATED APPLICATIONS

The present application is a continuation of U.S. patent application Ser. No. 16/273,529, filed Feb. 12, 2019, which is a continuation of U.S. patent application Ser. No. 14/263,996, filed Apr. 28, 2014, issued as U.S. Pat. No. 10,206,629 on Feb. 19, 2019, which is a continuation of U.S. patent application Ser. No. 13/532,346, filed Jun. 25, 2012, issued as U.S. Pat. No. 8,727,982 on May 20, 2014, which is a continuation of U.S. patent application Ser. No. 11/462,974 filed, Aug. 7, 2006, issued as U.S. Pat. No. 8,206,296 on Jun. 26, 2012, entitled "Method and System for Providing Integrated Analyte Monitoring and Infusion System Therapy Management", the disclosures of each of which are incorporated herein by reference in their entireties.

BACKGROUND

With increasing use of pump therapy for Type 1 diabetic patients, young and old alike, the importance of controlling the infusion device such as external infusion pumps is evident. Indeed, presently available external infusion devices typically include an input mechanism such as buttons through which the patient may program and control the infusion device. Such infusion devices also typically include a user interface such as a display which is configured to display information relevant to the patient's infusion progress, status of the various components of the infusion device, as well as other programmable information such as patient specific basal profiles.

The external infusion devices are typically connected to an infusion set which includes a cannula that is placed transcutaneously through the skin of the patient to infuse a select dosage of insulin based on the infusion device's programmed basal rates or any other infusion rates as prescribed by the patient's doctor. Generally, the patient is able to control the pump to administer additional doses of insulin during the course of wearing and operating the infusion device such as for, administering a carbohydrate bolus prior to a meal. Certain infusion devices include food database that has associated therewith, an amount of carbohydrate, so that the patient may better estimate the level of insulin dosage needed for, for example, calculating a bolus amount.

However, in general, most estimation or calculation of a bolus amount for administration, or a determination of a suitable basal profile, for that matter, are educated estimates based on the patient's physiology as determined by the patient's doctor, or an estimate performed by the patient. Moreover, the infusion devices do not generally include enhancement features that would better assist the diabetic patients to control and/or manage the glucose levels.

In view of the foregoing, it would be desirable to have a method and system for providing insulin therapy determination and recommendation based on real time monitored analyte levels of the patient for proactive insulin therapy treatment to improve management of diabetes.

SUMMARY OF THE INVENTION

In accordance with the various embodiments of the present invention, there are provided method and system for receiving data associated with monitored analyte related levels for a predetermined time period substantially in real time, retrieving one or more therapy profiles associated with the monitored analyte related levels, generating one or more modifications to the retrieved one or more therapy profiles based on the data associated with the monitored analyte related levels.

These and other objects, features and advantages of the present invention will become more fully apparent from the following detailed description of the embodiments, the appended claims and the accompanying drawings.

DETAILED DESCRIPTION

As described in detail below, in accordance with the various embodiments of the present invention, there are provided various embodiments for providing real time or substantially real time monitored levels associated with a patient's analyte levels, and one or more associated therapy recommendation associated with the monitored analyte levels to provide real time insulin therapy and management. Accordingly, in one embodiment of the present invention, diabetic patients may better control the glucose levels and improve their physiological conditions based on accurate and substantially real time monitoring of glucose levels, and are provided with one or more recommendations for modifying or maintaining the insulin therapy (based on, for example, insulin pump therapy), for real time proactive management of glucose levels.

Figure 1:
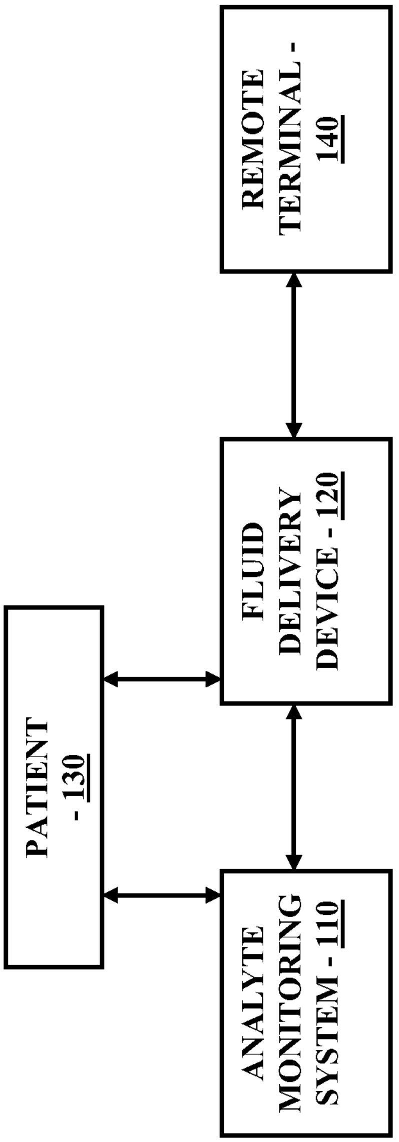
FIG. 1 is a block diagram illustrating an insulin therapy management system in accordance with one embodiment of the present invention.

FIG. 1 is a block diagram illustrating an insulin therapy management system for practicing one embodiment of the present invention. Referring to FIG. 1, the therapy management system 100 includes an analyte monitoring system 110 operatively coupled to a fluid delivery device 120, which may be in turn, operatively coupled to a remote terminal 140. As shown in the Figure, the analyte monitoring system 110 is, in one embodiment, coupled to the patient 130 so as to monitor or measure the analyte levels of the patient. Moreover, the fluid delivery device 120 is coupled to the patient using, for example, an infusion set and tubing connected to a cannula (not shown) that is placed transcutaneously through the skin of the patient so as to infuse medication such as, for example, insulin, to the patient.

Referring to FIG. 1, in one embodiment the analyte monitoring system 110 in one embodiment may include one or more analyte sensors subcutaneously positioned such that at least a portion of the analyte sensors are maintained in fluid contact with the patient's analytes. The analyte sensors may include, but are not limited to short term subcutaneous analyte sensors or transdermal analyte sensors, for example, which are configured to detect analyte levels of a patient over a predetermined time period, and after which, a replacement of the sensors is necessary.

The one or more analyte sensors of the analyte monitoring system 110 is coupled to a respective one or more of a data transmitter unit which is configured to receive one or more signals from the respective analyte sensors corresponding to the detected analyte levels of the patient, and to transmit the information corresponding to the detected analyte levels to a receiver device, and/or fluid delivery device 120. That is, over a communication link, the transmitter units may be configured to transmit data associated with the detected analyte levels periodically, and/or intermittently and repeatedly to one or more other devices such as the insulin delivery device and/or the remote terminal 140 for further data processing and analysis.

The transmitter units of the analyte monitoring system 110 may in one embodiment, be configured to transmit the analyte related data substantially in real time to the fluid delivery device 120 and/or the remote terminal 140 after receiving it from the corresponding analyte sensors such that the analyte level such as glucose level of the patient 130 may be monitored in real time. In one aspect, the analyte levels of the patient may be obtained using one or more discrete blood glucose testing devices such as blood glucose meters, or continuous analyte monitoring systems such as continuous glucose monitoring systems.

Additional analytes that may be monitored, determined or detected by the analyte monitoring system 110 include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Moreover, within the scope of the present invention, the transmitter units of the analyte monitoring system 110 may be configured to directly communicate with one or more of the remote terminal 140 or the fluid delivery device 120. Furthermore, within the scope of the present invention, additional devices may be provided for communication in the analyte monitoring system 110 including additional receiver/data processing unit, remote terminals (such as a physician's terminal and/or a bedside terminal in a hospital environment, for example. In addition, within the scope of the present invention, one or more of the analyte monitoring system 110, the fluid delivery device 120 and the remote terminal 140 may be configured to communicate over a wireless data communication link such as, but not limited to a radio frequency (RF) communication link, Bluetooth®) communication link, infrared communication link, or any other type of suitable wireless communication connection between two or more electronic devices, which may further be uni-directional or bi-directional communication between the two or more devices. Alternatively, the data communication link may include wired cable connection such as, for example, but not limited to RS232 connection, USB connection, or serial cable connection.

Referring back to FIG. 1, in one embodiment, the analyte monitoring system 110 includes a strip port configured to receive a test strip for capillary blood glucose testing. In one aspect, the glucose level measured using the test strip may in addition, be configured to provide periodic calibration of the analyte sensors of the analyte monitoring system 110 to assure and improve the accuracy of the analyte levels detected by the analyte sensors.

Additional detailed description of the continuous analyte monitoring system, its various components including the functional descriptions of the sensor, transmitter unit, receiver unit, and remote terminal/data processing terminal are provided in U.S. Pat. No. 6,175,752 issued Jan. 16, 2001 entitled "Analyte Monitoring Device and Methods of Use", and in application Ser. No. 10/745,878 filed Dec. 26, 2003, issued as U.S. Pat. No. 7,811,231, entitled "Continuous Glucose Monitoring System and Methods of Use", each assigned to the Assignee of the present application.

Referring again to FIG. 1, the fluid delivery device 120 may include in one embodiment, but not limited to, an external infusion device such as an external insulin infusion pump, an implantable pump, a pen-type insulin injector device, an on-body patch pump, an inhalable infusion device for nasal insulin delivery, or any other type of suitable delivery system. In addition, the remote terminal 140 in one embodiment may include for example, a desktop computer terminal, a data communication enabled kiosk, a laptop computer, a handheld computing device such as a personal digital assistant (PDAs), or a data communication enabled mobile telephone.

Figure 2:
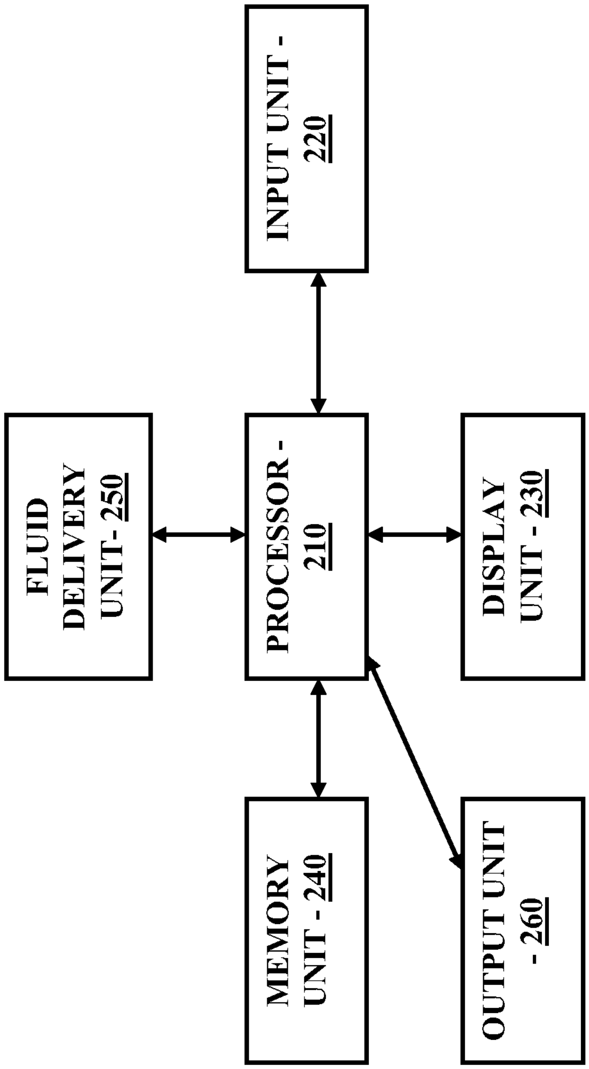
FIG. 2 is a block diagram illustrating the therapeutic fluid delivery device of FIG. 1 in accordance with one embodiment of the present invention.

FIG. 2 is a block diagram of an insulin delivery device of FIG. 1 in one embodiment of the present invention. Referring to FIG. 2, the fluid delivery device 120 in one embodiment includes a processor 210 operatively coupled to a memory unit 240, an input unit 220, a display unit 230, an output unit 260, and a fluid delivery unit 250. In one embodiment, the processor 210 includes a microprocessor that is configured to and capable of controlling the functions of the fluid delivery device 120 by controlling and/or accessing each of the various components of the fluid delivery device 120. In one embodiment, multiple processors may be provided as a safety measure and to provide redundancy in case of a single processor failure. Moreover, processing capabilities may be shared between multiple processor units within the insulin delivery device 120 such that pump functions and/or control may be performed faster and more accurately.

Referring back to FIG. 2, the input unit 220 operatively coupled to the processor 210 may include a jog dial, key pad buttons, a touch pad screen, or any other suitable input mechanism for providing input commands to the fluid delivery device 120. More specifically, in case of a jog dial input device, or a touch pad screen, for example, the patient or user of the fluid delivery device 120 will manipulate the respective jog dial or touch pad in conjunction with the display unit 230 which performs as both a data input and output units. The display unit 230 may include a touch sensitive screen, an LCD screen, or any other types of suitable display unit for the fluid delivery device 120 that is configured to display alphanumeric data as well as pictorial information such as icons associated with one or more predefined states of the fluid delivery device 120, or graphical representation of data such as trend charts and graphs associated with the insulin infusion rates, trend data of monitored glucose levels over a period of time, or textual notification to the patients.

Referring to FIG. 2, the output unit 260 operatively coupled to the processor 210 may include audible alarm including one or more tones and/or preprogrammed or programmable tunes or audio clips, or vibratory alert features having one or more pre-programmed or programmable vibratory alert levels. In one embodiment, the vibratory alert may also assist in priming the infusion tubing to minimize the potential for air or other undesirable material in the infusion tubing. Also shown in FIG. 2 is the fluid delivery unit 250 which is operatively coupled to the processor 210 and configured to deliver the insulin doses or amounts to the patient from the insulin reservoir or any other types of suitable containment for insulin to be delivered (not shown) in the fluid delivery device 120 via an infusion set coupled to a subcutaneously positioned cannula under the skin of the patient.

Referring yet again to FIG. 2, the memory unit 240 may include one or more of a random access memory (RAM), read only memory (ROM), or any other types of data storage units that is configured to store data as well as program instructions for access by the processor 210 and execution to control the fluid delivery device 120 and/or to perform data processing based on data received from the analyte monitoring system 110, the remote terminal 140, the patient 130 or any other data input source.

Figure 3:
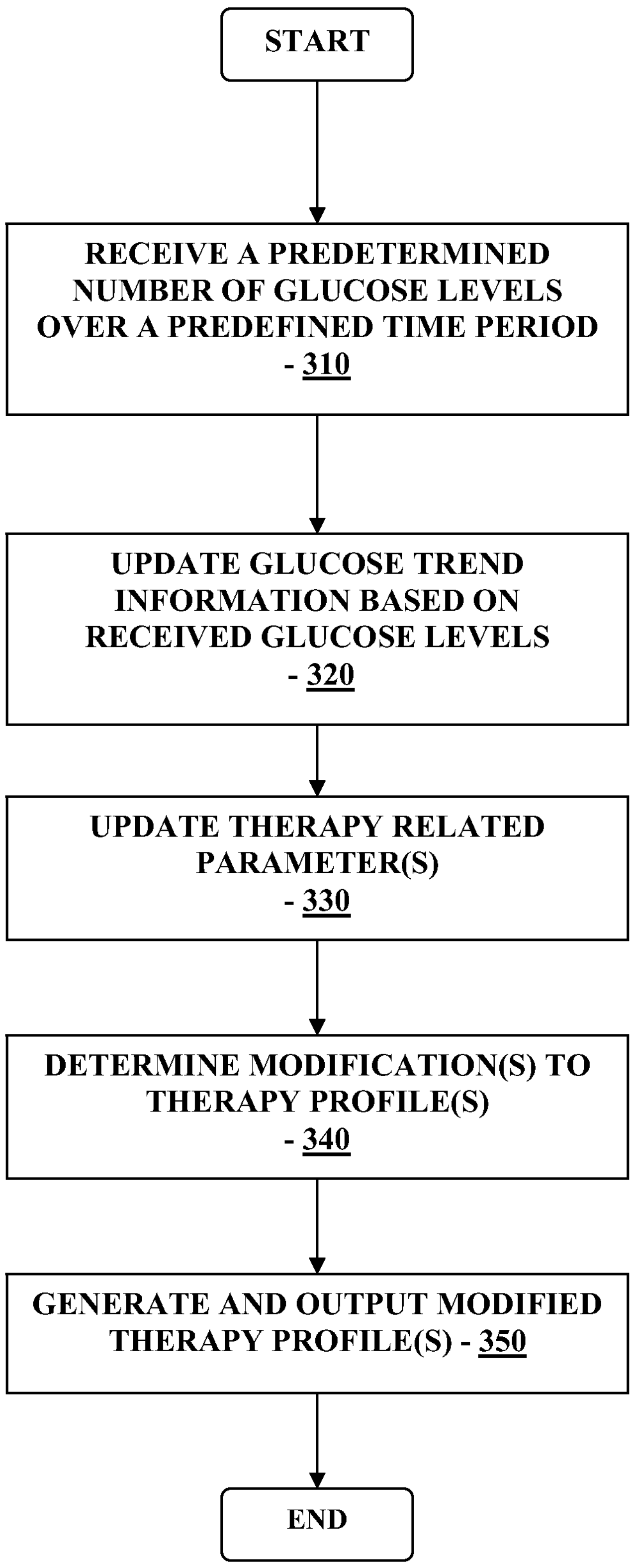
FIG. 3 is a flow chart illustrating a therapy management procedure based on real time monitored analyte levels in accordance with one embodiment of the present invention.

FIG. 3 is a flow chart illustrating insulin therapy management procedure based on real time monitored analyte levels in accordance with one embodiment of the present invention. Referring to FIG. 3, in one embodiment of the present invention, a predetermined number of consecutive glucose levels are received or detected over a predetermined or defined time period (310). For example, in one embodiment, referring to FIG. 1, the monitored glucose levels of a patient is substantially continuously received or detected substantially in real time for a predetermined time period. In one embodiment, the predefined time period may include one or more time periods, the data within which may provide a therapeutically meaningful basis for associated data analysis.

That is, the predefined time period of the real time monitored glucose data in one embodiment may include one or more time periods sufficient to provide glucose trend information or sufficient to provide analysis of glucose levels to adjust insulin therapy on an on-going, and substantially real time basis. For example, the predefined time period in one embodiment may include one or more of a 30 minute time period, a 45 minute time period, a one hour time period, a two hour time period and a 6 hour time period. While exemplary predefined time periods are provided herein, within the scope of the present invention, any suitable predefined time period may be employed as may be sufficient to be used for glucose trend determination and/or therapy related determinations (such as, for example, modification of existing basal profiles, calculation of temporary basal profile, or determination of a bolus amount).

Referring back to FIG. 3, the consecutive glucose levels received over the predefined time period in one embodiment may not be entirely consecutive due to, for example, data transmission errors and/or one or more of potential failure modes associated with data transmission or processing. As such, in one embodiment of the present invention, there is provided a predetermined margin of error for the received real time glucose data such that, a given number of data points associated with glucose levels which are erroneous or alternatively, not received from the glucose sensor, may be ignored or discarded.

Referring back to FIG. 3, upon receiving the predetermined number of glucose levels over a predefined time period, the glucose trend information based on the received glucose levels is updated (320). For example, in one embodiment, the glucose trend information estimating the rate of change of the glucose levels may be determined, and based upon which the projected level of glucose may be calculated. Indeed, in one embodiment, the glucose trend information may be configured to provide extrapolated glucose level information associated with the glucose level movement based on the real time glucose data received from the glucose sensor. That is, in one embodiment, the real time glucose levels monitored are used to determine the rate at which the glucose levels is either increasing or decreasing (or remaining substantially stable at a given level). Based on such information and over a predetermined time period, a glucose projected information may be determined.

Referring again to FIG. 3, the therapy related parameters associated with the monitored real time glucose levels is updated (330). That is, in one embodiment, one or more insulin therapy related parameters of an insulin pump such as including, but not limited to, insulin on board information associated with the fluid delivery device 120 (FIG. 1), insulin sensitivity level of the patient 130 (FIG. 1), insulin to carbohydrate ratio, and insulin absorption rate. Thereafter, in one embodiment, one or more modifications to the current therapy profile are determined (340). That is, in one embodiment of the present invention, one or more current basal profiles, calculated bolus levels, temporary basal profiles, and/or any other suitable pre-programmed insulin delivery profiles stored in the fluid delivery device 120 (FIG. 1) for example, are retrieved and analyzed based on one or more of the received real time glucose levels, the updated glucose trend information, and the updated therapy related parameters.

Referring back to FIG. 3, after determining one or more modifications to the therapy profiles, the modified one or more therapy profiles is generated and output to the patient 130 (FIG. 1) (350) so that the patient 130 may select, store and/or ignore the one or more modified therapy profiles based on one or more of the monitored real time glucose values, updated glucose trend information, and updated therapy related parameters.

For example, in one embodiment, the patient 130 may be provided with a recommended temporary basal profile based on the monitored real time glucose levels over a predetermined time period as well as the current basal profile which is executed by the fluid delivery device 120 (FIG. 1) to deliver a predetermined level of insulin to the patient 130 (FIG. 1). Alternatively, the patient 130 in a further embodiment may be provided with one or more additional recommended actions for selection as the patient sees suitable to enhance the insulin therapy based on the real time monitored glucose levels. For example, the patient may be provided with a recommended correction bolus level based on the real time monitored glucose levels and the current basal profile in conjunction with, for example, the patient's insulin sensitivity and/or insulin on board information.

In this manner, in one embodiment of the present invention, based on real time monitored glucose levels, the patient may be provided with on-going, real time insulin therapy options and modifications to the pre-programmed insulin delivery basal profiles so as to improve upon the initially programmed therapy profiles based on the monitored real time glucose data.

Figure 4:
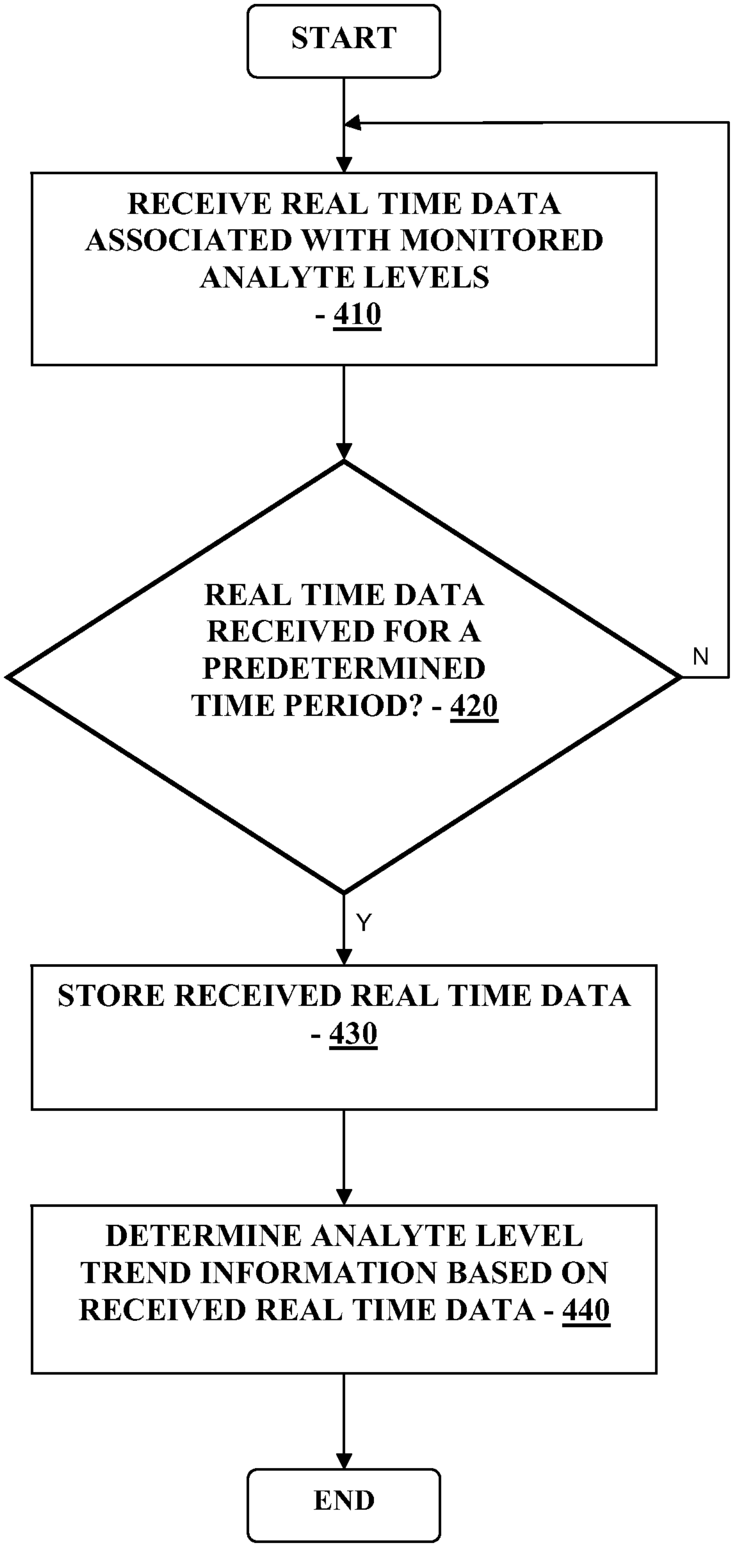
FIG. 4 is a flowchart illustrating an analyte trend information updating procedure based on real time monitored analyte levels in accordance with one embodiment of the present invention.

FIG. 4 is a flowchart illustrating analyte trend information updating procedure based on real time monitored analyte levels in accordance with one embodiment of the present invention. Referring to FIG. 4, in one embodiment, real time data associated with monitored analyte levels is received (410). Thereafter it is determined whether the real time data has been received for a predetermined time period (420). If it is determined that the real time data has not been received for at least the predetermined time period, then the routine continues to receive the real time data associated with the monitored analyte levels such as glucose levels.

On the other hand, referring back to FIG. 4, if it is determined that the real time data associated with the monitored analyte levels have been received for the predetermined time period (for example, as described above in conjunction with FIG. 3), then, the received real time data associated with the monitored analyte levels is stored (430). Thereafter, analyte level trend information is determined based on the received real time data associated with the monitored analyte levels (440).

For example, in one embodiment, the real time data associated with the monitored analyte levels is analyzed and an extrapolation of the data based on the rate of change of the monitored analyte levels is determined. That is, the real time data associated with the monitored analyte levels is used to determined the rate at which the monitored analyte level changed over the predetermined time period, and accordingly, a trend information is determined based on, for example, the determined rate at which the monitored analyte level changed over the predetermined time period.

In a further embodiment, the trend information based on the real time data associated with the monitored analyte levels may be dynamically modified and continuously updated based on the received real time data associated with the monitored analyte levels for one or more predetermined time periods. As such, in one embodiment, the trend information may be configured to dynamically change and be updated continuously based on the received real time data associated with the monitored analyte levels.

Figure 5:
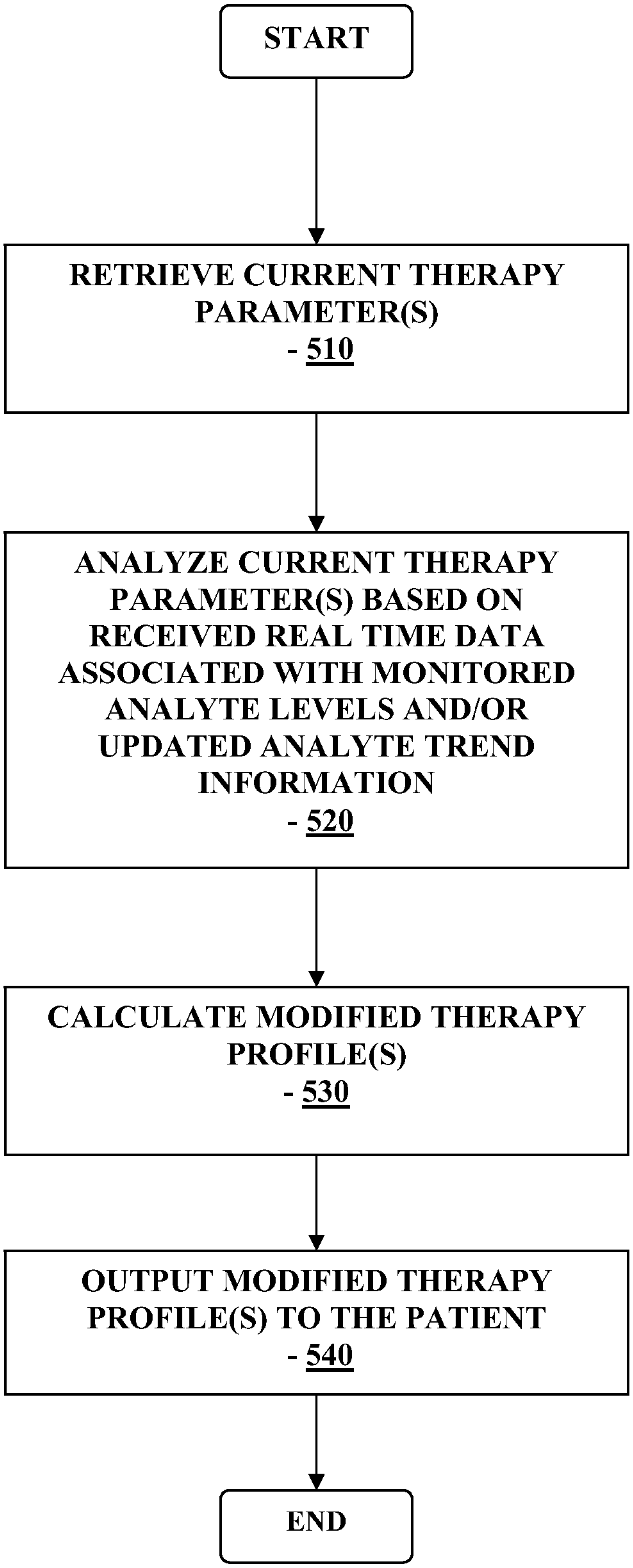
FIG. 5 is a flowchart illustrating a modified therapy management procedure based on real time monitored analyte levels in accordance with one embodiment of the present invention.

FIG. 5 is a flowchart illustrating modified therapy management procedure based on real time monitored analyte levels in accordance with one embodiment of the present invention. Referring to FIG. 5, in one embodiment, the current therapy parameters are retrieved (510) and, the retrieved current therapy parameters are analyzed based on the received real time data associated with the monitored analyte levels and/or updated analyte trend information (520). For example, one or more preprogrammed basal profiles, correction bolus, carbohydrate bolus, temporary basal and associated parameters are retrieved and analyzed based on, for example, the received real time data associated with the monitored analyte levels and/or updated analyte trend information, and further, factoring in the insulin sensitivity of the patient as well as insulin on board information.

Referring to FIG. 5, based upon the analysis of the current therapy parameters, one or more modified therapy profiles are calculated (530). That is, based upon the real time glucose levels monitored by the analyte monitoring system 110 (FIG. 1), a modification or adjustment to the pre-programmed basal profiles of the fluid delivery device 120 (FIG. 1) may be determined, and the modified therapy profiles are output to the patient 130 (FIG. 1) (540). That is, the modification or adjustment to the pre-programmed basal profiles may be provided to the patient for review and/or execution to implement the recommended modification or adjustment to the pre-programmed basal profiles.

In this manner, the patient may be provided with one or more adjustments to the existing or current basal profiles or any other pre-programmed therapy profiles based on continuously monitored physiological levels of the patient such as analyte levels of the patient. Indeed, in one embodiment of the present invention, using continuously monitored glucose levels of the patient, modification or adjustment to the pre-programmed basal profiles may be calculated and provided to the patient for review and implementation as desired by the patient. In this manner, for example, a diabetic patient may improve the insulin therapy management and control.

Within the scope of the present invention, the processes and routines described in conjunction with FIGS. 3-5 may be performed by the analyte monitoring system 110 (FIG. 1) and/or the fluid delivery device 120 (FIG. 1). Furthermore, the output of information associated with the modified therapy parameters, trend information, and/or real time data associated with the monitored analyte levels may be displayed on a display unit of the receiver of the analyte monitoring system 110 (FIG. 1), or the infusion device display of the fluid delivery device 120 (FIG. 1) or both. Alternatively, one or more such information may be output to the patient audibly as sound signal output.

In this manner, in accordance with the various embodiments of the present invention, there are provided methods and system for providing information associated with the direction and rate of change of analyte (e.g., glucose) levels for determination of, for example, bolus or basal rate change recommendations, for comparing expected glucose level changes to actual real time glucose level changes to update, for example, insulin sensitivity factor in an ongoing basis, and for automatically confirming the monitored glucose values within a preset time period (e.g., 30 minutes) after insulin therapy initiation to determine whether the initiated therapy is having the intended therapeutic effect.

Indeed, in accordance with the various embodiments of the present invention, the use of glucose trend information in insulin delivery rate determinations provides for a more accurate insulin dosing and may lead to a decrease in hypoglycemic events and improved HbA1Cs.

Accordingly, a method in one embodiment of the present invention includes receiving data associated with monitored analyte related levels for a predetermined time period substantially in real time, retrieving one or more therapy profiles associated with the monitored analyte related levels, generating one or more modifications to the retrieved one or more therapy profiles based on the data associated with the monitored analyte related levels.

The method may further include displaying the generated one or more modifications to the retrieved one or more therapy profiles.

In one aspect, the generated one or more modifications to the retrieved one or more therapy profiles may be displayed as one or more of an alphanumeric output display, a graphical output display, an icon display, a video output display, a color display or an illumination display.

In a further aspect, the predetermined time period may include a time period between 15 minutes and six hours.

The one or more therapy profiles in yet another aspect may include a basal profile, a correction bolus, a temporary basal profile, an insulin sensitivity, an insulin on board level, and an insulin absorption rate.

In still another aspect, retrieving the one or more therapy profiles associated with the monitored analyte related levels may include retrieving a current analyte rate of change information.

In yet still another aspect, generating the one or more modifications to the retrieved one or more therapy profiles may include determining a modified analyte rate of change information based on the received data associated with monitored analyte related levels.

Moreover, the method may further include generating an output alert based on the modified analyte rate of change information.

Still, the method may also include determining an analyte level projection information based on the modified analyte rate of change information.

A system for providing diabetes management in accordance with another embodiment of the present invention includes an interface unit, one or more processors coupled to the interface unit, a memory for storing instructions which, when executed by the one or more processors, causes the one or more processors to receive data associated with monitored analyte related levels for a predetermined time period substantially in real time, retrieve one or more therapy profiles associated with the monitored analyte related levels, and generate one or more modifications to the retrieved one or more therapy profiles based on the data associated with the monitored analyte related levels.

The interface unit may include an input unit and an output unit, the input unit configured to receive the one or more analyte related data, and the output unit configured to output the one or more of the generated modifications to the retrieved one or more therapy profiles.

The interface unit and the one or more processors in a further embodiment may be operatively coupled to one or more of a housing of an infusion device or a housing of an analyte monitoring system.

The infusion device may include one of an external insulin pump, an implantable insulin pump, an on-body patch pump, a pen-type injection device, an inhalable insulin delivery system, and a transdermal insulin delivery system.

The memory in a further aspect may be configured for storing instructions which, when executed by the one or more processors, causes the one or more processors to display the generated one or more modifications to the retrieved one or more therapy profiles.

Further, the memory may be configured for storing instructions which, when executed by the one or more processors, causes the one or more processors to display the generated one or more modifications to the retrieved one or more therapy profiles as one or more of an alphanumeric output display, a graphical output display, an icon display, a video output display, a color display or an illumination display.

In one aspect, the predetermined time period may include one of a time period between 15 minutes and six hours.

The one or more therapy profiles may include a basal profile, a correction bolus, a temporary basal profile, an insulin sensitivity, an insulin on board level, and an insulin absorption rate.

In another aspect, the memory may be further configured for storing instructions which, when executed by the one or more processors, causes the one or more processors to retrieve a current analyte rate of change information.

In still another aspect, the memory may be further configured for storing instructions which, when executed by the one or more processors, causes the one or more processors to determine a modified analyte rate of change information based on the received data associated with monitored analyte related levels.

Additionally, in yet still another aspect, the memory may be further configured for storing instructions which, when executed by the one or more processors, causes the one or more processors to generate an output alert based on the modified analyte rate of change information.

Further, the memory may be further configured for storing instructions which, when executed by the one or more processors, causes the one or more processors to determine an analyte level projection information based on the modified analyte rate of change information.

A system for providing diabetes management in accordance with yet another embodiment of the present invention includes an analyte monitoring system configured to monitor analyte related levels of a patient substantially in real time, a medication delivery unit operatively for wirelessly receiving data associated with the monitored analyte level of the patient substantially in real time from the analyte monitoring system, a data processing unit operatively coupled to the one or more of the analyte monitoring system or the medication delivery unit, the data processing unit configured to retrieve one or more therapy profiles associated with the monitored analyte related levels, and generate one or more modifications to the retrieved one or more therapy profiles based on the data associated with the monitored analyte related levels.

In one aspect, the analyte monitoring system may be configured to wirelessly communicate with the medication delivery unit over a radio frequency (RF) communication link, a Bluetooth® communication link, an Infrared communication link, or a local area network (LAN).

The various processes described above including the processes performed by the processor 210 in the software application execution environment in the fluid delivery device 120 as well as any other suitable or similar processing units embodied in the analyte monitoring system 110 and the remote terminal 140, including the processes and routines described in conjunction with FIGS. 3-5, may be embodied as computer programs developed using an object oriented language that allows the modeling of complex systems with modular objects to create abstractions that are representative of real world, physical objects and their interrelationships. The software required to carry out the inventive process, which may be stored in the memory unit 240 (or similar storage devices in the analyte monitoring system 110 and the remote terminal 140) of the processor 210, may be developed by a person of ordinary skill in the art and may include one or more computer program products.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

The invention claimed is:

1. A system for automatically updating a basal insulin profile, the system comprising:
- a glucose monitoring system, comprising:
  - a glucose sensor comprising a portion configured to be placed subcutaneously in contact with a bodily fluid of a user, and
  - a data transmitter unit configured to receive signals from the glucose sensor and to transmit information corresponding to real-time glucose levels; and
- an insulin delivery device in wireless communication with the glucose monitoring system and configured to deliver insulin to the user, wherein the insulin delivery device comprises a processor coupled to a memory storing instructions that, when executed by the processor, cause the processor to:
  - retrieve a basal insulin profile and one or more insulin therapy parameters from the memory, wherein the one or more insulin therapy parameters comprise insulin on board and an insulin sensitivity factor, receive real-time glucose levels from the data transmitter unit, determine a rate of change of the glucose levels over a predetermined time period based on the real-time glucose levels, determine an updated basal insulin delivery rate based on a previously administered insulin profile, the real-time glucose levels, and the rate of change of the glucose levels, generate an updated basal insulin profile, wherein the updated basal insulin profile includes the updated basal insulin delivery rate, cause administration of insulin according to the updated basal insulin delivery rate; and output a recommendation for a correction bolus on a display, wherein the recommendation is based on the real-time glucose levels and the one or more insulin therapy parameters.

2. The system of claim 1, wherein the insulin delivery device comprises an infusion pump.

3. The system of claim 2, wherein the infusion pump comprises an infusion set and a cannula configured to be placed through a skin of the user.

4. The system of claim 1, wherein the insulin delivery device is in wireless communication with the glucose monitoring system by a Bluetooth communication protocol.

5. The system of claim 1, wherein the glucose monitoring system comprises a strip port configured to receive a test strip for testing blood glucose levels.

6. The system of claim 5, wherein the blood glucose levels are used to calibrate the glucose sensor.

7. The system of claim 1, wherein the processor is configured to cause administration of insulin according to the updated basal insulin delivery rate upon receipt of an input from the user to execute the updated basal insulin profile.

8. The system of claim 1, wherein the one or more insulin therapy parameters are updated based on the rate of change of the glucose levels.

9. The system of claim 1, wherein the processor is further caused to determine a projected glucose level based on the rate of change of the glucose levels.

10. The system of claim 1, further comprising adjusting at least one of the one or more insulin therapy parameters, wherein the one or more insulin therapy parameters that are adjusted comprises the insulin sensitivity factor.

11. The system of claim 1, wherein the predetermined time period is 15 minutes to 6 hours.

12. The system of claim 1, wherein the basal insulin profile is a pre-programmed basal insulin profile.

13. A method for automatically updating a basal insulin profile, the method comprising:

collecting signals by a glucose monitoring system comprising a glucose sensor having a portion placed subcutaneously in contact with a bodily fluid of a user;

transmitting information corresponding to real-time glucose levels by a data transmitter unit that receives signals from the glucose sensor;

retrieving, by a processor of an insulin delivery device in wireless communication with the glucose monitoring system, a basal insulin profile and one or more insulin therapy parameters from a memory coupled to the processor, wherein the one or more insulin therapy parameters comprise insulin on board and an insulin sensitivity factor;

receiving, by the processor, real-time glucose levels from the data transmitter unit;

determining, by the processor, a rate of change of the glucose levels over a predetermined time period based on the real-time glucose levels;

determining, by the processor, an updated basal insulin delivery rate based on the basal insulin profile, the real-time glucose levels, and the rate of change of the glucose levels;

generating an updated basal insulin profile that includes the updated basal insulin delivery rate;

causing, by the processor, administration of insulin according to the updated basal insulin delivery rate; and outputting a recommendation for a correction bolus on a display, wherein the recommendation is based on the real-time glucose levels and the one or more insulin therapy parameters.

14. The method of claim 13, wherein the insulin delivery device comprises an infusion pump.

15. The method of claim 13, wherein the information corresponding to real-time glucose levels is transmitted by the data transmitter unit to the insulin delivery device via a Bluetooth communication protocol.

16. The method of claim 13, further comprising adjusting at least one of the one or more insulin therapy parameters, wherein the one or more insulin therapy parameters that are adjusted comprises the insulin sensitivity factor.

17. The method of claim 13, further comprising receiving a test strip in a strip port of the glucose monitoring system, and measuring a blood glucose level using the test strip.

18. The method of claim 17, further comprising calibrating the glucose sensor using the blood glucose level measured using the test strip.

19. The method of claim 13, further comprising receiving an input from the user to execute the updated basal insulin profile prior to causing administration of insulin according to the updated basal insulin delivery rate.

20. The method of claim 13, further comprising outputting an alert based on the rate of change of the glucose levels.

* * * * *